US007063865B2

(12) United States Patent
Jones et al.

(10) Patent No.: US 7,063,865 B2
(45) Date of Patent: Jun. 20, 2006

(54) COMPOSITION AND METHOD FOR SUBSTANTIALLY REDUCING THE DELETERIOUS EFFECTS OF ALCOHOL ON THE BODY

(76) Inventors: Jeremy Park Jones, 1702 E. Laura La., Tempe, AZ (US) 85283; Peter Kevin Dobler, 5845 E. Indian School Rd., Phoenix, AZ (US) 85018

( * ) Notice: Subject to any disclaimer, the term of this patent is extended or adjusted under 35 U.S.C. 154(b) by 406 days.

(21) Appl. No.: 10/144,155

(22) Filed: May 10, 2002

(65) Prior Publication Data
US 2003/0211172 A1 Nov. 13, 2003

(51) Int. Cl.
- *A61K 31/28* (2006.01)
- *A61K 31/51* (2006.01)
- *A61K 33/00* (2006.01)
- *A61K 33/24* (2006.01)
- *A61P 3/02* (2006.01)

(52) U.S. Cl. ............ 424/646; 424/639; 424/641; 424/643; 424/655; 424/675; 424/678; 424/681; 424/682; 424/683; 424/686; 424/687; 424/692; 424/693; 424/696; 424/697; 424/702; 424/715; 424/716; 424/717; 514/52; 514/263.31; 514/263.34; 514/276; 514/345; 514/474; 514/492; 514/494; 514/505; 514/554; 514/556; 514/557; 514/561; 514/562; 514/574; 514/706; 514/904; 514/905; 514/922; 514/974; 426/72; 426/73; 426/74

(58) Field of Classification Search ............... 514/52, 514/263.31, 263.34, 276, 345, 474, 492, 514/494, 505, 554, 556, 557, 561–562, 574, 514/706, 904, 905, 922, 974; 424/639, 641, 424/643, 646, 655, 675, 678, 681–683, 686–687, 424/692, 693, 696–697, 702, 715–717; 426/72, 426/74, 73
See application file for complete search history.

(56) References Cited

U.S. PATENT DOCUMENTS 6,103,756 A * 8/2000 Gorsek ................. 514/458

FOREIGN PATENT DOCUMENTS

| WO | 00/57726 | * | 10/2000 |
| WO | 02/12882 | * | 2/2002 |

* cited by examiner

*Primary Examiner*—John Pak

(57) ABSTRACT

A composition that will substantially reduce the deleterious effects of alcohol on the body and substantially reduce the side effects associated with hangovers (i.e. headaches, dizziness, nausea, dry mouth, etc) when taken as recommended. The composition includes an effective amount of (I)-glycine, (I)-glutathione, thiamine, magnesium, selenium, molybdenum. Other vitamins, mineral compounds, flavoring, coloring, and solubility agents may also be added.

6 Claims, No Drawings

COMPOSITION AND METHOD FOR SUBSTANTIALLY REDUCING THE DELETERIOUS EFFECTS OF ALCOHOL ON THE BODY

FIELD OF THE INVENTION

This invention relates to a composition that taken as recommended will substantially reduce the deleterious effects of alcohol on the body and substantially reduce the side-effects associated with hangovers (i.e. headaches, dizziness, nausea, dry mouth, etc).

BACKGROUND OF THE INVENTION

Alcohol intoxication causes dehydration and an imbalance in electrolytes, minerals, and some vitamins in the bloodstream, disrupting many normal biological processes. In addition, if the level of alcohol is high in the blood, the liver becomes backed up and the enzymes responsible for detoxification then utilize secondary pathways of detoxification thereby producing toxic metabolites. These metabolites are much more toxic than alcohol and can cause nausea, headaches, and discomfort, usually collectively referred to as a "hangover." It has also been suggested that congeners worsen hangovers. "Congeners" are toxic byproducts of distillation and fermentation. Some spirits are higher in congeners than others. For example, red wine, brandies, and whiskies are usually higher than other types of alcohol.

Hangovers have been plaguing mankind since time immemorial. The best approach to hangovers is to avoid them by not over imbibing in alcohol in the first place. This however is easier said that done. Hangovers are typically characterized by a throbbing headache, an upset stomach with nausea, dizziness and dry mouth. In addition to these physical consequences, hangovers have staggering economic and societal consequences. Billions of dollars are lost in the workplace due to low productivity and absenteeism. Moreover, people with hangovers experience diminished cognitive abilities that may pose a substantial threat to themselves and others, particularly in the workplace and while driving.

Folk remedies for hangovers abound and include more of the liquor that caused the hangover (aka "hair of the dog"), a Bloody Mary, aspirin and more sleep, a lot of water, a long, hot shower, and coffee made with tonic water, orange juice and honey. Most of these are administered after the fact. However, if one already has a hangover resulting from overindulging in alcohol, the damage has already been done. A lot of morning-after hangover remedies have been tried, but there's not much evidence they help. Moreover, it is inconvenient for the person suffering from a hangover to have to get up and go shopping for some of these purported remedies when they least feel like doing so.

Remedies such as "coating the stomach" with milk and/or bread and butter before drinking to slow the absorption of alcohol have also not been shown to stave off hangovers. Moreover, such items may not be readily available before drinking begins. They also supply an abundance of extra calories, and may contribute to later nausea.

Accordingly, there has been a need for another weapon in the armamentarium against hangovers. There is a still further need for a novel composition to substantially prevent hangovers that are effective, convenient, and healthy. There is an additional need for a novel composition that make a night out more fun without having to worry about how one is going to feel the next day. There is a further need for a novel composition to substantially reduce the effects of alcohol on the body. There is an additional need for a novel composition that provides the chemicals the liver needs to facilitate detoxification and excretion of alcohol and to lower the toxic metabolite concentrations in the blood thereby substantially reducing side effects. There is a still further need for a composition to prepare and support the body for alcohol intoxication. The present invention fulfills each of these needs and also provides other related advantages.

SUMMARY OF THE INVENTION

The composition generally comprises an effective amount of each of (I)-glycine, (1)-glutathione, thiamine, magnesium, selenium, molybdenum. In a first preferred embodiment, the embodiment comprises an effective amount of each of (I)-glycine, (I)-glutathione, at least one magnesium compound, of at least one selenium compound, at least one molybdenum compound, and thiamine (Vitamin B1). In a second preferred embodiment, additional mineral and vitamin compounds may be added to the composition. In a third embodiment, coloring and flavoring agents may be added. By using the composition with alcoholic beverages as recommended the persons using the composition will substantially reduce the deleterious effects of alcohol on the body and substantially reduce the side-effects associated with hangovers (i.e. headaches, dizziness, nausea, dry mouth, etc).

Other features and advantages of the present invention will become apparent from the following more detailed description.

DETAILED DESCRIPTION OF THE PREFERRED EMBODIMENTS

The present invention is concerned with a composition that will substantially reduce the deleterious effects of alcohol on the body and substantially reduce the side-effects associated with hangovers (i.e. headaches, dizziness, nausea, dry mouth, etc) when used as recommended. The composition in the first embodiment is comprised of effective amounts of each of the following: (I)-glycine, (I)-glutathione, thiamine (Vitamin B1), magnesium, selenium, molybdenum. In the first preferred embodiment, the composition in 4 g comprises:

| Ingredient Name | Amount | Active Amount | Range of Active Sub. |
|---|---|---|---|
| (I)-Glutathione | 25 mg | 25 mg | 5–250 mg |
| (I)-Glycine | 1,000 mg | 1,000 mg | 100 mg–2 g |
| Magnesium Compound(s) | 38 mg | 7.2 mg | 3–800 mg |
| Molybdenum Compound(s) | 25 mg | 50 µg | 25–250 µg |
| Selenium Compound(s) | 17 mg | 33 µg | 10–200 µg |
| Thiamine Compound(s) | 12 mg | 12 mg | 2–20 mg |

Organic chelations or bacteria/yeast digested mineral/vitamin compounds are preferred because of their greater bioavailability, and solubility.

Additional vitamins, mineral compounds, and solubility agents may be used within the confines of the invention in a second preferred embodiment. The second preferred embodiment is a composition comprising the following compounds (ingredients) in the amounts per 4 g is as shown on the next page:

| Ingredient Name | Amount | Active amount |
| --- | --- | --- |
| Ascorbic Acid | 200 mg | 200 mg |
| Calcium Compound(s) | 170 mg | 15 mg |
| Chromium Compound(s) | 367 μg | 40 μg |
| Cyanocobalamin | 5 mg | 50 μg |
| (l)-Glutathione | 25 mg | 25 mg |
| (l)-Glycine | 1,000 mg | 1,000 mg |
| Magnesium Compound(s) | 38 mg | 7.2 mg |
| Manganese Compound(s) | 3.6 mg | 1 mg |
| Molybdenum Compound(s) | 25 mg | 50 μg |
| Pyridoxine Compound(s) | 28 mg | 13 mg |
| Selenium Compound(s) | 17 mg | 33 μg |
| Potassium Hydrogen Carbonate | 300 mg | 5 mg |
| Tartaric Acid | 400 mg | 400 mg |
| Thiamine Compound(s) | 35 mg | 17 mg |
| Zinc Compound(s) | 34 mg | 5 mg |

The third preferred embodiment comprises in 4 g the following:

| Ingredient Name | Amount | Active amount |
| --- | --- | --- |
| Ascorbic Acid | 200 mg | 200 mg |
| Caffeine | 35 mg | 35 mg |
| Calcium Compound(s) | 170 mg | 15 mg |
| Chromium Compound(s) | 367 μg | 40 μg |
| Coloring Agent | Variant | |
| Cyanocobalamin | 5 mg | 50 μg |
| Flavor Agents | Variant | |
| (l)-Glutathione | 25 mg | 25 mg |
| (l)-Glycine | 1.000 mg | 1,000 mg |
| Magnesium Compound(s) | 38 mg | 7.2 mg |
| Manganese Compound(s) | 3.6 mg | 1 mg |
| Molybdenum Compound(s) | 25 mg | 50 μg |
| Potassium Hydrogen Carbonate | 300 mg | 5 mg |
| Pyridoxine Compound(s) | 28 mg | 13 mg |
| Selenium Compound(s) | 17 mg | 33 μg |
| Sugar | Variant | |
| Tartaric Acid | 400 mg | 400 mg |
| Thiamine Compound(s) | 35 mg | 17 mg |
| Zinc Compound(s) | 34 mg | 5 mg |

These compounds and amounts of each substantially ensure maximum effect. Through investigation and research, the particular range of these substances of the compounds used, have been found to substantially reduce the deleterious effects of alcohol on the body, and substantially reduce the side-effects associated with hangovers (i.e. headaches, dizziness, nausea, dry mouth, etc).

The compounds used are as follows:

Ascorbic add (Vitamin C): This vitamin aids in norepinephrine synthesis. This is believed to be a valuable treatment into schizophrenia, chorea, and dyskinesia. We believe it aids in neurological function thereby being a cofactor with thiamine HCl in the reduction of alcohol induced Wernicke Korsakoff syndrome. Ascorbic acid is also an important buffer component in the Xo3 thereby affecting pH and increasing the absorption of many substances found in the Xo3.

Caffeine (1,3,7-trimethylxanthine): Is the number one desired stimulant in the US. People who drink alcohol or have high levels of (l)-glycine typically become more tired and need caffeine to give them stimulation. Alcohol drinkers have been shown to crave stimulants, like caffeine. In addition caffeine, in lower dosages, increase renal output thereby removing toxins, like alcohol and its metabolites, quicker.

Calcium Gluconate: This substance is an important buffering agent (see ascorbic acid) Calcium salts increase the pH, reducing acid indigestion from consuming low pH (3.0–4.1) alcohol containing beverages. In addition, Calcium gluconate aids in the function of neurotransmitters at synaptic junctions. Brain damage may be reduced with proper levels of calcium.

Chromium Nicotinate and Picolinate: A mixed form of these types of chromium aid in glucose tolerance by production of glucose tolerance factor (GTF). By aiding in this function, it minimizes the ability of alcohols to adversely effect glucose/insulin tolerance and may possibly reduce alcohol aggravated diabetes.

(l)-Glutathione: (l)-Glutathione acts as one of the major detoxifiers in the body. Selenium must be present for (l)-glutathione to be in its most active form as an antioxidant and detoxifying agent. (l)-Glutathione detoxifies the liver of aldehydes and ketones that build up upon alcohol and other toxic substance intake. It also helps remove heavy metal toxins from the body. Molybdenum is a cofactor in its usage. (l)-Glutathione also reduces liver disease including cirrhosis and fatty liver disease caused by alcohol.

(l)-Glycine: (l)-Glycine normalizes functional state of the nervous system and metabolic disorders, improve the redox processes in the lymphocytes changed under alcohol, and protects the body both on the metabolic and microstructural levels. It also tastes good.

Magnesium (mixed forms): The majority of magnesium is found in the mitochondria, the organelles that are responsible for oxidative phosphorylation producing ATP, a major chemical the body uses for almost all energetic reactions. A decreased dosage can result in heart problems, lack of energy, pore bone structure, muscle spasms and tightness. Alcohol reduces magnesium absorption. Therefore, it is believed to be beneficial that a person consuming alcohol supplement with organic, bioavailable forms of magnesium and manganese; as these two minerals work in conjuction in many mitochondria processes.

Manganese: This mineral helps protest against oxidative damage in the mitochondria by stimulating SOD (superoxide dismutase) activity. Oxidative damage is increased as toxins, such as alcohol, are increased.

Molybdenum: Mo functions as a co-factor for oxidative-reduction reactions. The enzymes involved are xanthine oxidase, aldehydye dehyrogenase, and sulfite oxidase. Aldehyde oxidase is an important enzyme primarily found in the liver. It is this enzyme that is responsible for the detoxification of alcohol. It is believed that Mo and Se work in conjunction in many antioxidant and detoxification reactions in the liver and kidneys.

Potassium Bicarbonate: This chemical with tartaric acid creates a fizzing action that modulates dissolution of the minerals. In addition, it provides the potassium cation (K), one of the most important cations in the body. The K/Na ratio is essential for regulating fluid balance in tissues. Alcohol consumption hampers proper fluid balance so an increase of K is beneficial. K also works in conjunction with Mg to aid in proper heart and muscle function. K is intimately involved in renal function. Renal function is an important detoxification process for alcohol.

Selenium: Selenium in conjunction with Mo is involved in the synthesis of the enzyme glutathione peroxidase (GP). GP consists of four subunit enzymes with one selenium per subunit in the form of selenocysteine. This enzyme (GP) is responsible for alcohol detoxification in the body. One important synergistic trio of the composition is Mo, Se, and (l)-glutathione. By adding these together in the proper ratios, alcohol breakdown in the human body is facilitated without excess production of aldehydes and other toxic metabolites in the bloodstream. These toxic metabolites are a major source of hangover symptoms.

Thiamine HCl (Vitamin B-1): Thiamine is the vitamin found to be most depleted by alcohol consumption. If a deficiency occurs, many alcohol induced neurological problems manifest (see ascorbic add).

Cobalamin (Vitamin B-12): The cyano-form is used to facilitate oral absorption. Cobalamin works in conjunction with Vitamins B-1 and B-6 to reduce alcohol induced neuralgias.

Pyridoxine (Vitamin B-6): Alcohol has been shown to cause B-6 depletion. Therefore it is important to adjunct the composition with vitamin B-6. B-6 depletion causes nausea, depression, vomiting, and peripheral neuritis.

Zinc: Zinc is regulated primarily by sulfur containing amino acids such as (I)-glutathione. Zinc is a cofactor with selenium and (1)-glutathione and other agents for alcohol metabolism. Deficiency can lead to alcoholism, and impaired alcohol induced glucose tolerance.

Agents such as citric acid, cellulose, magnesium stearate and silicone dioxide and other excipient agents may also be added.

The composition is manufactured according to Good Manufacturing Practices (GMP) as recommended by the National Nutritional Foods Association/FDA. For example, in order to make approximately 25,000 each containing 5 gram unit doses of the third preferred embodiment of the composition, the following exemplary batch sheet is provided

| PRODUCT: XO3 | | | |
|---|---|---|---|
| TOTAL MG | INGREDIENTS | CODE NO | KILOS |
| 206.19 | Ascorbic Acid | R034 | 5.155 |
| 35.00 | Caffeine | R881 | 0.875 |
| 166.67 | Calcium Gluconate | R115 | 4.167 |
| 0.17 | Chromium Picolinate | R153 | 0.004 |
| 0.20 | Chromium Poly Nicotinate | R857 | 0.005 |
| 60.00 | Flavor F-102498 | R1381 | 1.500 |
| 60.00 | Flavor F-118485 | R1382 | 1.500 |
| 22.00 | Glutathione Reduced | R1380 | 0.550 |
| 1000.00 | Glycine | R358 | 25.000 |
| 17.39 | Magnesium Malate 15.2% | R1383 | 0.435 |
| 40.00 | Magnesium Taurate | R1384 | 1.000 |
| 3.60 | Manganese Citrate 28% | R414 | 0.090 |
| 25.00 | Molybdenum Glycinate .2% | R1385 | 0.625 |
| 300.00 | Potassium Bicarbonate | R843 | 7.500 |
| 16.50 | Selenium AAC .2% | R547 | 0.413 |
| 2350.01 | Sugar | R211 | 58.750 |
| 400.00 | Tartaric Acid | R1392 | 10.000 |
| 12.44 | Vitamin B1 HCl | R628 | 0.311 |
| 30.91 | Vitamin B1 Mononitrate | R1329 | 0.773 |
| 5.00 | Vitamin B12 1% Trit. | R626 | 0.125 |
| 9.51 | Vitamin B6 HCL | R621 | 0.238 |
| 23.64 | Viamin B6 | R1327 | 0.591 |
| 33.33 | Zinc Arginate | R1253 | 0.833 |
| 50.00 | Citric Acid | R159 | 3.750 |
| 33.33 | Sodium Bicarbonate | R563 | 0.833 |
| 3.50 | COLOR | Customer Supplied | 0.088 |
| 5004.39 | | | 125.110 |

The composition is mixed by blending all components/ingredients without flavorings (including but not limited to sugar) for 30 minutes. The flavorings are blended separately for 30 minutes. The blended flavorings are then mixed with the balance of materials for 45 minutes. The final product yield is calculated by weight and staged for packaging.

All ingredients are purchased from reliable, long-term suppliers with proven track records. The mineral compounds are available from a supplier such as Kelatron, 1675 West 2750 South, Ogden, Utah.

Certificates of Analysis are verified versus a sample of the product by visual, odor, taste, identification (as per USP24 and FTIR) and any additional testing as needed, prior to raw material being released for use in manufacturing.

Manufacturing areas and methods are monitored by quality control staff while manufacturing is in process. In process, quality control visually inspects the composition being manufactured. The packaging areas and methods are monitored by quality control staff while packaging is in process. The packaging process is visually inspected every 15 minutes. Quality control staff verifies the quality of bulk containers by checking the fill weight every 15 minutes. The finished product is inspected for defects as it is being staged for final packaging and the product is spot checked as it is being placed into shipping containers (cartons or boxes).

In the method of the invention, the composition may be a powder, administered orally as a drink additive. The composition may be mixed with any consumable liquid, including the alcoholic beverage itself, or water, soft drinks, juices, etc. The suggested dose schedule is 2–3 packets of a unit dose over the course of a day/night before and during consumption of alcoholic beverages, starting about one hour prior to the first alcoholic beverage. Preferably, the 2–3 doses are taken prior to consuming 30 ml of ethanol (typically three drinks). The composition may of course be incorporated in other oral delivery methods, such as tablets, capsules, etc. by methods known to persons skilled in the art.

From the foregoing, it is to be appreciated that the composition when taken as recommended will substantially reduce the deleterious effects of alcohol on the body and substantially reduce the side-effects associated with hangovers (i.e. headaches, dizziness, nausea, dry mouth, etc). The preferred composition is a powdered drink additive designed to prepare and support the body, before and during consumption of alcoholic beverages.

Although a particular embodiment of the invention has been described in detail for purposes of illustration, various modifications may be made without departing from the spirit and scope of the invention. Accordingly, the invention is not to be limited, except as by the appended claims.

We claim:

1. A composition comprising:
   about 1 g to 2 g glycine;
   25 mg to 250 mg L-glutathione;
   3 mg to 800 mg magnesium;
   25 microgram to 250 microgram molybdenum;
   10 microgram to 200 microgram selenium; and
   2 mg to 20 mg thiamine (vitamin B1),
   wherein the composition, when consumed by a person before and/or during consumption of alcoholic beverages, substantially reduces the deleterious effects of alcohol on the body and substantially reduces the side-effects associated with a hangover selected from the group consisting of heache, dizziness, nausea and dry mouth.

2. The composition of claim 1, wherein a 4 g sample composition comprises 1 g of glycine, 25 mg of L-glutathione, 17 mg total thiamine (vitamin B1) compounds, 38 mg total magnesium compound(s), 25 microgram molybdenum, and 17 microgram selenium, wherein the composition, when consumed by a person before and/or during consumption of alcoholic beverages, substantially reduces the deleterious effects of alcohol on the body and substantially reduces the side-effects associated with a hangover selected from the group consisting of heache, dizziness, nausea and dry mouth.

3. The composition of claim 1, wherein the active amount of L-glutathione is 25 mg, glycine is 1 g, magnesium is 7.2 mg, molybdenum is 50 microgram, selenium is 33 microgram, and thiamine (vitamin B1) is 17 mg.

4. The composition of claim 1, wherein the composition further comprises at least one calcium compound, at least one chromium compound, at least one manganese compound, at least one zinc compound, ascorbic acid, caffeine, potassium hydrogen carbonate, tartaric acid, at least one cobalamin compound (vitamin B12), and at least one pyridoxine compound (vitamin B6).

5. The composition of claim 1, further comprising an effective amount of at least one coloring agent, and/or at least one flavoring agent.

6. The composition of claim 1, wherein the composition is formulated to be taken orally.

* * * * *